United States Patent
Gross et al.

(10) Patent No.: US 8,410,778 B2
(45) Date of Patent: Apr. 2, 2013

(54) MAGNETIC RESONANCE METHOD AND APPARATUS TO ACQUIRE MULTIPLE IMAGE DATA SETS FROM A SUBJECT

(75) Inventors: Patrick Gross, Langensendelbach (DE); Joerg Roland, Hemhofen (DE)

(73) Assignee: Siemens Aktiengesellschaft, Munich (DE)

( * ) Notice: Subject to any disclaimer, the term of this patent is extended or adjusted under 35 U.S.C. 154(b) by 346 days.

(21) Appl. No.: 12/722,559

(22) Filed: Mar. 12, 2010

(65) Prior Publication Data

US 2010/0231217 A1    Sep. 16, 2010

(30) Foreign Application Priority Data

Mar. 12, 2009    (DE) .................. 10 2009 012 851

(51) Int. Cl.
*G01R 3/00* (2006.01)
*A61B 5/055* (2006.01)

(52) U.S. Cl. ........ 324/309; 324/307; 324/315; 324/316; 600/410

(58) Field of Classification Search .......... 324/300–322; 600/407–464; 382/128–131
See application file for complete search history.

(56) References Cited

U.S. PATENT DOCUMENTS

| | | | | |
|---|---|---|---|---|
| 4,684,891 A * | 8/1987 | Feinberg | ............... | 324/309 |
| 5,422,576 A | 6/1995 | Kao et al. | | |
| 5,711,300 A * | 1/1998 | Schneider et al. | ............ | 600/412 |
| 6,501,272 B1 | 12/2002 | Haacke et al. | | |
| 8,242,780 B2 * | 8/2012 | Geppert et al. | ............... | 324/309 |
| 2002/0183612 A1 * | 12/2002 | Deimling | ...................... | 600/410 |
| 2006/0064002 A1 | 3/2006 | Grist et al. | | |
| 2011/0092801 A1 * | 4/2011 | Gross et al. | .................. | 600/412 |

* cited by examiner

*Primary Examiner* — Melissa Koval
*Assistant Examiner* — Emily Chan
(74) *Attorney, Agent, or Firm* — Schiff Hardin LLP

(57) ABSTRACT

In a magnetic resonance (MR) method and apparatus for the acquisition of a first image data set and a second image data set of an examination subject, a series of excitation pulses is radiated into the examination subject, and after each excitation pulse, a first echo signal is detected after a first echo time TE1 and a second echo signal is detected after a second echo time TE2, with TE2 greater than TE1, and the first echo signal is entered in a first raw MR data set and the second echo signal is entered in a second raw MR data set. A first image data set is acquired from the first MR data set on the basis of magnitude information contained in the first MR data set. A second image data set is acquired from the second MR data set on the basis of phase information contained in the second MR data set. The first and second image data sets are stored on at least one memory device.

This manner of data acquisition and processing delivers results that typically are obtained from two different data acquisition and processing procedures, one for each desired image data set.

10 Claims, 3 Drawing Sheets

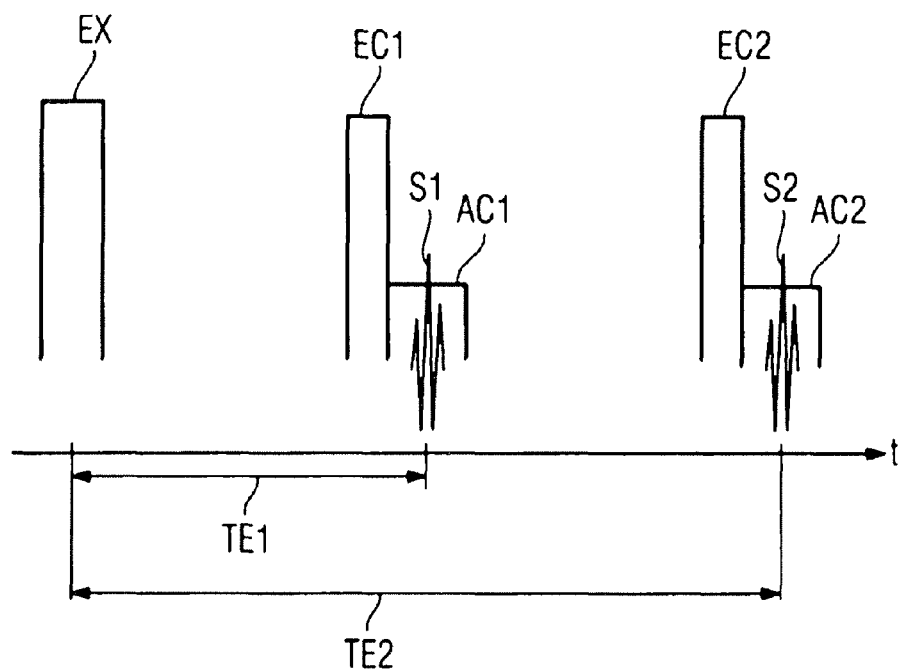

MAGNETIC RESONANCE METHOD AND APPARATUS TO ACQUIRE MULTIPLE IMAGE DATA SETS FROM A SUBJECT

BACKGROUND OF THE INVENTION

1. Field of the Invention

The invention concerns a method, a magnetic resonance apparatus, a computer-readable data medium to acquire a first image data set and a second image data set of an examination subject by means of magnetic resonance.

2. Description of the Prior Art

Magnetic resonance (MR) is a known modality with which images of the inside of an examination subject can be generated. Described in a simplified way, the examination subject is positioned in a strong, static, homogeneous basic magnetic field (field strengths of 0.2 Tesla to 7 Tesla or more) in a magnetic resonance data acquisition unit so that nuclear spins in a subject orient along the basic magnetic field. To excite nuclear magnetic resonances, radio-frequency excitation pulses are radiated into the examination subject, the excited nuclear magnetic resonance signals are measured, and anatomical MR images (for example) are reconstructed based on these signals. For spatial coding of the measurement data, rapidly switched magnetic gradient fields are overlaid on the basic magnetic field. The recorded measurement data are digitized and stored in a k-space matrix as complex numerical values (raw data). An MR image can be reconstructed from the k-space matrix populated with such values by means of a multidimensional Fourier transformation. In addition to anatomical images, spectroscopy data, movement data or temperature data of an examined or treated area can be determined by magnetic resonance techniques.

An additional field of application of magnetic resonance is monitoring procedures or treatments, for example endoscopic procedures or radiation therapy treatments. Particularly in the case of ablation of tumor tissue—for example by means of high intensity focused ultrasound (HIFU)—MR temperature imaging is increasingly being used in order to determine the predominant temperatures in a treated area with optimally high precision and with high time resolution during the treatment.

For optimal monitoring during a treatment or a procedure, not only should the temperature in the treated area be measured with time and spatial resolution, but the relation of the measured temperature images to the anatomy of the patient should be known.

An MR technique that is frequently applied for temperature imaging is known as the proton resonance frequency method, which is based on the evaluation of the phases of the complex raw MR data. In contrast to this, anatomical information is most often obtained from the magnitude (absolute value of the amplitude) of the complex raw MR data. The respective data sets are normally measured separately.

It is possible in principle to retroactively register temperature data acquired from an MR measurement with anatomy data acquired with a separate MR measurement. However, this is complicated, error-prone and time-consuming. In order to avoid these problems, temperature images and anatomical images that were acquired from one and the same echo signal of a measurement are shown overlaid. An additional registration thus is not needed since the two images were obtained from the same data. However, the result of such overlaid images has not always been satisfactory in the past since the quality of the temperature images and the anatomical images can not be simultaneously optimized. In particular, the echo times for optimal temperature images are markedly longer than for anatomical images obtained from magnitude information. The same applies with regard to other anatomical images obtained from magnitude information with regard to registered MR images (for example flow images).

Another method in order to at least save time in the separate acquisition of the two images is the use of acquisition techniques that reduce the acquisition time, for example partial Fourier acquisition or a reduction of the resolution in the phase coding direction for the acquisition of the anatomical images. However, this generally leads to a degradation of the image quality since these methods are particularly susceptible to interference, in particular due to patient movements.

SUMMARY OF THE INVENTION

An object of the present invention to provide a method, a magnetic resonance apparatus, and a computer-readable medium that allow two image data sets of an examination subject to be acquired in an optimally short time period, wherein each of the acquired image data sets is of high quality.

A method according to the invention for the acquisition of a first image data set and a second image data set of an examination subject includes the following steps. A series of excitation pulses are radiated into the examination subject, each excitation pulse causing emission from the subject of a first echo signal after a first echo time TE1 and a second echo signal after a second echo time TE2, with TE2 greater than TE1. The first echo signal is detected and entered into a first raw MR data set and the second echo signal is detected and entered into a second raw MR data set. A first image data set is calculated from the first MR data set on the basis of magnitude information contained in the first MR data set, and a second image data set is calculated from the second MR data set on the basis of phase information contained in the second MR data set. The first and second image data sets are stored in least one memory device.

With the method, measurement values (echo signals) for different image data sets (for example one image data set obtained from magnitude information with regard to anatomy and an image data set with regard to temperature or flow or anatomy, possibly with different contrast, obtained from phase information on) are thus acquired after each excitation pulse. In this way a measurement with the method according to the invention delivers results that typically had to be collected from two different measurements, one for each desired image data set.

By setting the second echo time to be greater than the first echo time, optimal results for the first image data set and the second image data set are achieved. A long echo time is particularly suitable for the acquisition of raw MR data from which image data should be obtained on the basis of phase information. A short echo time is suitable for the acquisition of raw MR data from which image data should be obtained on the basis of magnitude information. The echo times can selected so that the total measurement duration of the method according to the invention for the acquisition of both the first image data set and the second image data set with high quality does not exceed the measurement duration of an equivalent measurement to acquire only a second image data set.

Moreover, there is no necessity to register the two acquired image data sets with one another since they are already registered (in registration) with one another by the acquisition of the first and second raw MR data in a readout train after a common excitation pulse.

Particularly in connection with a real-time temperature determination with sufficient time resolution by means of MR for a qualitative assessment of tumor ablations, in which a simultaneous monitoring of the anatomy for an estimation of possible movements of the patient can be relevant to safety, the method can be used profitably since it both reduces the total measurement time and enables a high quality of the temperature images and anatomy images. Moreover, an improved registration of the temperature images with planning images acquired before the tumor ablation is also enabled via the anatomy images acquired simultaneously with the temperature images.

Typical sequence protocols for thermoablations allow the acquisition of multiple echoes with short TE without lengthening the acquisition time of the sequence, and are therefore amendable to the inventive method.

A magnetic resonance apparatus according to the invention for the acquisition of a first image data set and a second image data set of an examination subject has a basic field magnet that generates a basic magnetic field in an examination volume of a magnetic resonance scanner, gradient coils that generate gradient fields in the examination volume, a gradient coil control unit that controls the gradient coils, and therefore the generated gradient fields, a radio-frequency transmitter that generates radio-frequency signals, a receiver unit that receives radio-frequency magnetic resonance (echo) signals from the examination volume, radio-frequency antennas to radiate radio-frequency signals generated by the radio-frequency transmitter into the examination volume and that acquire and relay the radio-frequency magnetic resonance (echo) signals from the examination volume to the receiver unit, a control device that controls the gradient coil control unit, the receiver unit and the radio-frequency transmitter, at least one computer that evaluates the received radio-frequency signals to obtain image data sets from the radio-frequency signals and a presentation device to display the acquired image data sets, wherein the control unit is configured to operate the above components to implement the method described above.

The invention also encompasses an electronically readable data medium that is encoded with electronically readable control information (programming instructions) stored in electronically readable data medium, the control information causing a computer or control device to implement the method according to the invention when the data medium is loaded in a control device of a magnetic resonance apparatus.

BRIEF DESCRIPTION OF THE DRAWINGS

FIG. 3 schematically illustrates an exemplary pulse sequence scheme that can be used for the method according to the invention,

DESCRIPTION OF THE PREFERRED EMBODIMENTS

Figure 1:
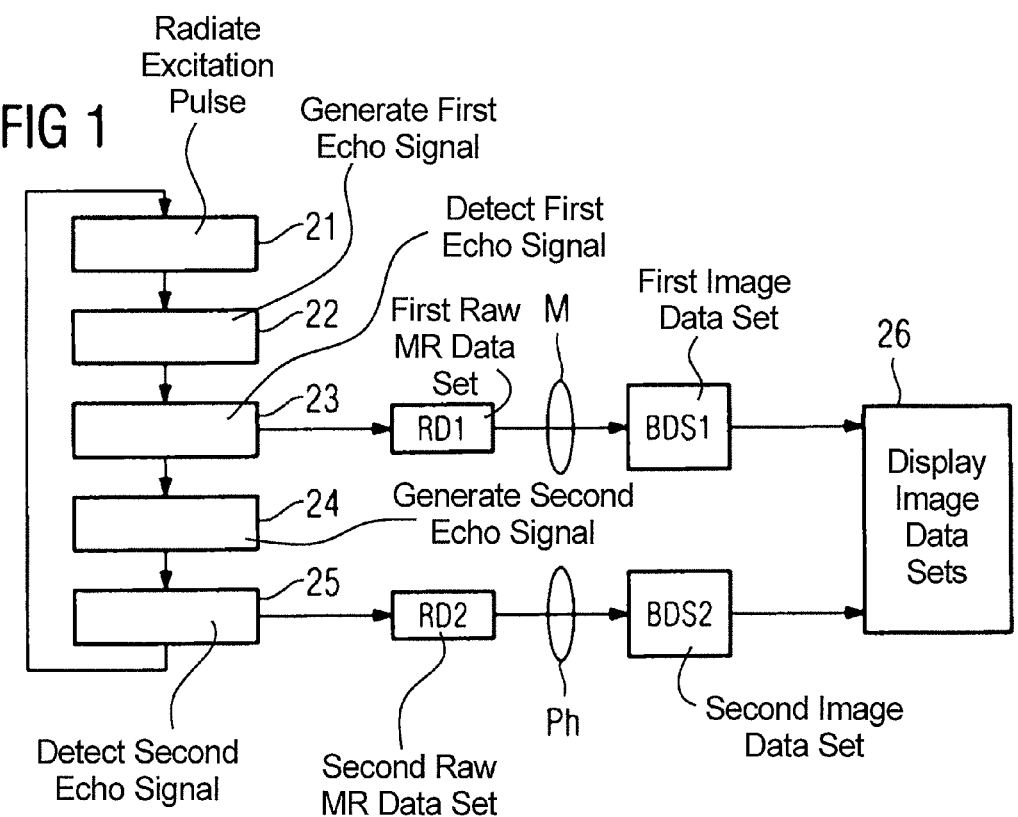
FIG. 1 is a flowchart of an embodiment of the method according to the invention.
Figure 2:
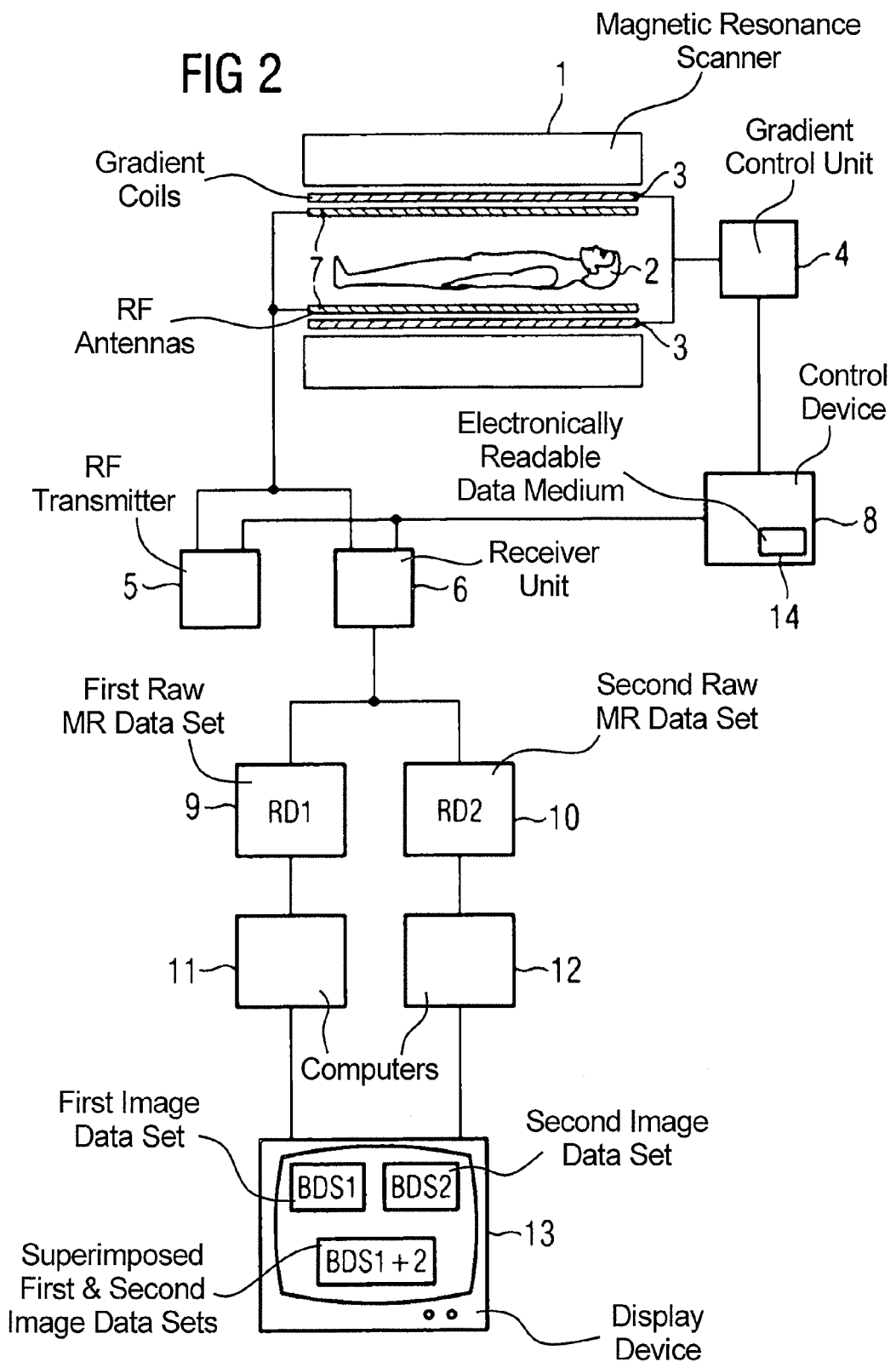
FIG. 2 schematically illustrates an embodiment of the magnetic resonance apparatus according to the invention.

FIG. 1 is a flowchart that illustrates the method according to the invention for the acquisition of a first image data set (designated with "BDS1") and a second image data set (designated with "BDS2") of an examination subject, for example a patient 2 (see FIG. 2).

An excitation pulse is radiated into the examination subject (Block 21). After the excitation pulse, a first echo signal is generated (Block 22) and detected (Block 23) at a first echo time TE1. The detected first echo signal is stored in a first raw MR data set (designated with "RD1"). A second echo signal is generated (Block 24) and detected (Block 25) at a second echo time TE2. The detected second echo signal is thereby stored in a second raw MR data set (designated with "RD2"). TE2 is greater than TE1. This sequence from excitation pulse (Block 21) through detection of the second echo signal (Block 25) is repeated until a sufficient number of first and second echo signals exist in the first or, respectively, second raw MR data set.

For example, echo signals that correspond to one or more lines of the respective raw MR data set (RD1, RD2) are acquired during a pass of the cited sequence from Block 21 through Block 25 and the sequence from Block 21 through Block 25 is repeated until a desired number of lines in the respective raw MR data set has been acquired.

A first image data set BDS1 is obtained from the stored first raw MR data set on the basis of magnitude information (designated with "M") contained there. A second image data set BDS2 is obtained from the stored second raw MR data set on the basis of phase information (designated with "Ph") contained there.

The acquisition of the first and second image data sets BDS1 and BDS2 does not have to be done exclusively on the basis of the magnitude information from the first raw MR data set and phase information from the second raw MR data set. Additional data can also be used for this purpose. For example, calibration data or correction data could be used in order to reduce artifacts in the first and second image data sets BDS1 and BDS2. Furthermore, it is possible for multiple first and multiple second echo signals to also be generated and detected after an excitation pulse, with the detected, first echo signals stored in the first raw MR data set and the detected, second echo signals stored in the second raw MR data set.

The two acquired image data sets BDS1 and BDS2 are superimposed and/or displayed separately (Block 26; see also FIG. 2).

The echo signals are advantageously generated by gradient pulses. Such echo signals (also called gradient echoes) enable a fast generation and detection of echo signals.

The first echo signal and also the second echo signal can each be only one echo signal, or can be a train of echo signals. For the latter case, use of the known echo planar imaging (EPI) sequence (in particular a segmented EPI sequence) is particularly advantageous, for example. Multiple lines of each raw MR data set can be detected in a short time period in this way, without reducing the quality of the raw data contained in the raw MR data sets.

In the method according to the invention, two different image data sets are thus obtained from different raw MR data sets, in particular with different echo times TE1 and TE2, within one measurement.

As noted above, it already results through the acquisition of the two image data sets according to the invention that the image data sets are spatially registered precisely with one another. This can also be advantageously utilized, for example in connection with MR phase contrast-based flow imaging, which shows a flow (for example of blood) in context with the surrounding anatomy. Furthermore, the phase imaging is also used to show anatomy in connection with magnetic resonance apparatuses with higher basic magnetic field strengths (for example as of 7 T). The method according to the invention thus can be used advantageously used in order to show two anatomy image data sets with differently optimized contrasts, namely one in a phase-optimized manner and the other in a magnitude-optimized manner.

The first image data set thus represents an anatomical image, and the second image data set represents a temperature image or a flow image whose depiction of the functionality (temperature or flow) can be placed in the context of the anatomy with the aid of the first image data set and the "automatic" registration. Furthermore, the second image data set can represent an additional anatomical image, wherein additional information can be obtained from the different contrasts of the first and second image data set.

A magnetic resonance system with which the pulse sequence according to the invention is applied is schematically depicted in FIG. 2. A patient 2 is located in the basic field magnet of a scanner (MR data acquisition unit) 1. Gradient coils 3 and radio-frequency (RF) antennas 7 are also provided in the scanner 1.

The radio-frequency antennas 7 are connected both to a radio-frequency transmitter 5 and a receiver unit 6. The gradient coils 3 are charged with current by a gradient control unit 4.

The gradient control unit 4, the radio-frequency transmitter 5 and the radio-frequency antennas 6 are operated by a control device 8. Two types of signals are obtained in the receiver unit 6 by corresponding activation according to the pulse sequences described above and explained in further detail below. These signals are digitized and stored in respective separate memory devices 9 and 10. For example, the control device 8 can be operated by the use of an electronically readable data medium 14 (with electronically readable control information stored (encoded) therein) loaded in the control unit. The control information is designed to cause the aforementioned method to be implemented by the magnetic resonance apparatus. Computers 11 and 12, which essentially implement a multidimensional Fourier transformation and possibly an absolute value calculation, obtain image information in the form of image data sets BDS1, BDS2 from the raw data in the form of the raw MR data sets RD1 and RD2 in the memory devices 9 and 10, and store this image information in the memory devices 9, 10. In the case of the first raw MR data set RD1, this occurs on the basis of magnitude information contained in the first raw MR data set; in the case of the second raw MR data set, this occurs on the basis of phase information contained in the second raw MR data set.

This image information can be presented separately or in overlaid mode on a display device 13 (for example a monitor). The magnetic resonance apparatus is thus designed such that the method described above can be implemented. In particular, the components of the magnetic resonance apparatus—for instance the control device 8, the gradient control unit 4, the receiver unit 6 and the computers 11, 12—are suitably configured to cooperatively radiate a series excitation pulses into the patient 2; generate and detect, in first and second raw MR data sets, a first echo signal after a first echo time TE1 and a second echo signal after a second echo time TE2 after every excitation pulse; and to obtain a first image data set from the first raw MR data set on the basis of magnitude information contained therein and a second image data set from the second raw MR data set on the basis of phase information contained therein.

The separation of the memory devices 9 and 10 and the computers 11 and 12 in the depiction in FIG. 2 serves as an illustration of the conceptual units. The memory devices 9 and 10 and the computers 11 and 12 can actually be arbitrarily physically distributed, in particular they can be combined in one unit.

An exemplary pulse sequence that can be used for the method according to the invention is shown in FIG. 3. The sequence of radio-frequency and gradient pulses that are radiated to excite and determine the nuclear magnetic resonance signals in the examination subject is designated as a pulse sequence.

The pulse scheme of FIG. 3 has an excitation pulse (designated with "EX") plotted over time t, after which follows a first echo pulse (designated with "EC1") that generates a first echo signal (designated with "S1") after a first echo time (designated with "TE1"). The first echo signal is read out by a first readout pulse (designated with "AC1"). A second echo pulse (designated with "EC2") generates a second echo signal (designated with "S2") after an echo time (designated with "TE2", with TE2 greater than TE1) The second echo signal is read out by a second readout pulse (designated with "AC2").

In a simple exemplary embodiment, exactly one line of a raw MR data set matrix is detected during the pulse scheme shown in FIG. 3. This means that the pulse scheme with adapted gradients is repeated 128 times for a matrix with 128×128 entries until the raw MR data set matrix has been completely acquired.

Typical first echo times are in a range of approximately 3 milliseconds; typical second echo times are in a range of approximately 13 milliseconds.

Alternatively, multiple lines of the matrix can be acquired per first or second echo signal within a shown pulse schematic, for example by means of echo planar imaging (EPI), wherein a train of echo signals is generated as a first and/or second echo signal instead of only one echo signal. The repetition of the pulse scheme can be correspondingly reduced. For example, if four lines of the matrix are acquired within one shown pulse scheme (thus after one excitation pulse), 32 repetitions are already sufficient to completely acquire the matrix. If three lines are acquired per, 43 repetitions are sufficient etc.

Although modifications and changes may be suggested by those skilled in the art, it is the intention of the inventor to embody within the patent warranted hereon all changes and modifications as reasonably and properly come within the scope of their contribution to the art.

We claim as our invention:

1. A magnetic resonance method for acquiring a first image data set and a second image data set from an examination subject, comprising the steps of:

placing an examination subject in a magnetic resonance data acquisition unit and, from said magnetic resonance data acquisition unit, radiating a plurality of excitation pulses into the examination subject;

operating said magnetic resonance data acquisition unit to generate, after each excitation pulse, a first echo signal after a first echo time TE1 and a second echo signal after a second echo time TE2, with TE2 being longer than TE1;

detecting said first echo signal and entering said first echo signal in a first raw magnetic resonance data set, and detecting said second echo signal and entering said second echo signal in a second raw magnetic resonance data set that is separate from said first raw magnetic resonance data set;

in a processor, acquiring a first image data set that is separate from said first image data set, from the first raw magnetic resonance data set based on magnitude information contained in the first raw magnetic resonance data set;

in said processor, acquiring a second image data set from the second raw magnetic resonance data set based on phase information contained in the second raw magnetic resonance data set; and storing said first and second image data sets in at least one memory device in a form allowing access to said first and second image data sets.

2. A method as claimed in claim 1 comprising displaying said first image data set and said second image data set at a display device having access to said at least one memory device, in a displayed mode selected from the group consisting of separately displaying said first image data set and said second image data set, and superimposed display of said first image data set and said second image data set.

3. A method as claimed in claim 1 comprising generating said first and second echo signals by emitting respective gradient pulses in said magnetic resonance data acquisition unit.

4. A method as claimed in claim 1 comprising detecting each of said first and second echo signals respectively as an individual echo signal or as a train of echo signals.

5. A method as claimed in claim 1 comprising generating said echo signals by operating said magnetic resonance data acquisition unit according to an echo planar imaging sequence.

6. A method as claimed in claim 5 comprising generating said first and second echo signals by operating said magnetic resonance data acquisition unit with a segmented echo planar imaging sequence.

7. A method as claimed in claim 1 comprising acquiring said first image data set as an anatomical image from said first raw magnetic resonance data set.

8. A method as claimed in claim 1 comprising acquiring said second image data set as an image selected from the group consisting of a temperature image, a flow image, and an anatomical image, from said second raw magnetic resonance data set.

9. A magnetic resonance apparatus comprising:
a magnetic resonance data acquisition unit comprising a basic field magnet that generates a basic magnetic field in an examination volume of the data acquisition unit;
gradient coils in said data acquisition unit that generate gradient fields in the examination volume;
a gradient coil unit that controls the gradient coils to generate said gradient fields;
a radio-frequency transmitter that generates radio-frequency signals;
a radio-frequency antenna system connected to said radio-frequency transmitter that radiates said radio-frequency signals into an examination subject located in said examination volume of said data acquisition unit, and that acquire radio-frequency signals from the examination subject that result from the radiated radio-frequency signals;
a receiver unit connected to said antenna system that receives the detection radio-frequency signals;
a control device that operates said gradient coil control unit, said receiver unit and said radio-frequency transmitter, said control unit being configured to cause said radio-frequency transmitter and said antenna system to radiate a plurality of excitation pulses into the examination subject, and to operate said gradient control unit to generate, after each excitation pulse, a first echo signal after a first echo time TE1, and a second echo signal after second echo time TE2, with TE2 being longer than TE1, and to operate said radio-frequency antenna system and said receiver unit to detect the first echo signal and to enter the first echo signal in a first raw magnetic resonance data set, and to detect the second echo signal and to enter the second echo signal into a second raw magnetic resonance data set; and
a computer supplied with said first and second raw magnetic resonance data sets, said computer being configured to acquire a first image data from the first raw magnetic resonance data set based on magnitude information contained in the first raw magnetic resonance data set, and to acquire a second image data set from the second raw magnetic resonance data set based on phase information contained in the second raw magnetic resonance data set; and
a memory connected to said computer in which said computer stores said first and second image data sets.

10. A non-transitory computer-readable medium encoded with programming instructions, said medium being loaded into a computerized operating and data evaluation system of a magnetic resonance apparatus, and said programming instructions causing said computerized operating and data evaluation system to:
radiate a plurality of excitation pulses into an examination subject in a magnetic resonance data acquisition of said magnetic resonance apparatus;
operate said magnetic resonance data acquisition unit to generate, after each excitation pulse, a first echo signal after a first echo time TE1 and a second echo signal after a second echo time TE2, with TE2 being longer than TE1;
detect said first echo signal and entering said first echo signal in a first raw magnetic resonance data set, and detect said second echo signal and entering said second echo signal in a second raw magnetic resonance data set that is separate from said first raw magnetic resonance data set;
acquire a first image data set from the first raw magnetic resonance data set based on magnitude information contained in the first raw magnetic resonance data set;
acquire a second image data set that is separate from said first image data set, from the second raw magnetic resonance data set based on phase information contained in the second raw magnetic resonance data set; and
store said first and second image data sets in at least one memory device in a form allowing access to said first and second image data sets.

* * * * *